US011102944B2

(12) United States Patent
Vardi

(10) Patent No.: US 11,102,944 B2
(45) Date of Patent: Aug. 31, 2021

(54) WATERMELON PLANTS WITH TOLERANCE TO POWDERY MILDEW

(71) Applicant: ORIGENE SEEDS LTD., Kibbutz Givat Brenner (IL)

(72) Inventor: Eyal A. Vardi, Rehovot (IL)

(73) Assignee: ORIGENE SEEDS LTD., Kibbutz Givat Brenner (IL)

(*) Notice: Subject to any disclaimer, the term of this patent is extended or adjusted under 35 U.S.C. 154(b) by 0 days.

(21) Appl. No.: 16/255,530

(22) Filed: Jan. 23, 2019

(65) Prior Publication Data
US 2019/0216035 A1 Jul. 18, 2019

Related U.S. Application Data

(60) Division of application No. 14/692,047, filed on Apr. 21, 2015, now Pat. No. 11,006,594, which is a continuation-in-part of application No. PCT/IL2013/050982, filed on Nov. 27, 2013.

(60) Provisional application No. 61/730,190, filed on Nov. 27, 2012.

(51) Int. Cl.
*A01H 6/34* (2018.01)
*A01H 1/04* (2006.01)
*A01H 1/00* (2006.01)
*A01H 5/08* (2018.01)

(52) U.S. Cl.
CPC ............... *A01H 6/342* (2018.05); *A01H 1/04* (2013.01); *A01H 1/045* (2021.01); *A01H 1/1255* (2021.01); *A01H 5/08* (2013.01)

(58) Field of Classification Search
None
See application file for complete search history.

(56) References Cited

U.S. PATENT DOCUMENTS 7,115,800 B2 * 10/2006 Barham .................... A01H 1/00 800/308
9,173,356 B2 † 11/2015 Tolla
2009/0133141 A1 5/2009 Zhang
2016/0029584 A1 * 2/2016 Tolla .......................... A01H 5/08 800/308

OTHER PUBLICATIONS

Bang et al, 2004, J. Hort. Sci. & Biotechnol. 79:885-890 (Year: 2004).*
Kano, 1991, Environ. Control in Biol. 4:159-166 (Year: 1991).*
Kano, 2004, J. Hort. Sci. & Biotechnol. 79:142-145 (Year: 2004).*
Davis et al (2007, J. Amer. Soc. Hort. Sci. 132:790-795) (Year: 2007).*
Ben-Naim et al., 2015, Phytopath.105:1446-1457 (Year: 2015).*
Farias-Larios et al, 1997, New Zealand J. Crop & Hort. Sci. 25:369-374 (Year: 1997).*
Buttrose et al, 1978, Ann. Bot. 42:599-608 (Year: 1978).*
Motsenbocker et al, 2002, HorTechnol. 12:437-440 (Year: 2002).*
Sundstrom et al, 1983, J. Amer. Soc. Hort. Sci. 108:879-881 (Year: 1983).*
Ben-Naim, 2010, The inheritance of resistance against powdery mildew *Sphaerotheca fuliginea* in watermelon *Citrullus anatus* (Thumb), Master's Degree Thesis; Bar Ilan University (Year: 2010).*
GRIN PI 482312, https://npgsweb.ars-grin.gov/gringlobal/accessiondetail?id=1377248, accessed Nov. 30, 2020.*
Davis AR, et al Watermelon resistance to powdery mildew race 1 and race 2. In G.J. Holmes (ed.) Proc. Cucurbitaceae. Universal Press, Raleigh, NC; 412-420 (2006).
Levi A, et al. "An extended linkage map for watermelon based on SRAP, AFLP, SSR, ISSR and RAPD markers". J Amer. Soc. Hort. Sci. 131(3): 393-402 (2006).
Levi A, et al. DNA markers from different linkage regions of watermelon genome useful in differentiating among closely related watermelon genotypes. HortScience 42(2): 210-214 (2007).
Pitrat M, et al Inheritance of Podosphaera xanthii resistance in melon line '90625'. Cucurbitacaea 2008, Proceeding of the IXth EUCAPRIA meeting on genetics and breeding of Cucurbitaceae, 135-142 (2008).
Robinson RW. et al. "Inheritance of susceptibility to powdery mildew in the watermelon" The J of Heredity 66:310-311 (1975).
Tettehy AY, "Identifying resistance to powdery mildew race 2W in the USDA—ARS watermelon germplasm collection". Crop Sci. 50: 933-393 (2010).
Zhang H, et al. "Sources of resistances to race 2WF powdery mildew in US watermelon plant introductions." HortScience, 46(10): 1349-1352 (2011).
De Queiroz et al.; "Genetic resources and watermelon breeding at Embrapa Semi-Arido" Crop Breeding and Applied Biotechnology; 1 ; 301-312 (2001).
De Franca Souza et al; "Heterotic effects in triploid watermelon hybrids" Crop Breeding and Applied Biotechnology;5 ; 280-286 (2005).
Tetteh, Breeding for Resistance to Powdery Mildew Race 2W in Watermelon. PhD Dissertation, North Carolina State University. (2008).
Cohen et al. "Cross-infectivity of Sphaerotheca fuliginea to watermelon, melon, and cucumber" Proc. Cucurbitaceae. 58-88 2000.
Davis et al. "Evaluation of Watermelon and Related Species for Resistance to Race 1W Powdery Mildew" J. Amer Soc. Sci. 132(6) 790-795 (2007).

(Continued)

Primary Examiner — Anne Kubelik
(74) Attorney, Agent, or Firm — Browdy and Neimark, PLLC

(57) ABSTRACT

The present disclosure concerns triploid hybrid watermelon plants characterized by a tolerance to powdery mildew (PM) and capable of producing seedless fruits with a total soluble solid (TSS) in the range of 10% to 13%, and a red fruit flesh. In some embodiments, the triploid plants are resistant to at least one of PM1 and PM2 races. The present disclosure also concerns seeds of said triploid watermelon plant, and any progeny of such plant. Further provided by the present disclosure is a diploid watermelon line having tolerance to PM and being capable of pollinating a tetraploid watermelon to produce a triploid hybrid, as well as the tetraploid watermelon and methods of producing said triploid plant from said diploid and tetraploid plants.

13 Claims, 6 Drawing Sheets
Specification includes a Sequence Listing.

(56) References Cited

OTHER PUBLICATIONS

Thomas et al. "Evaluation of U.S. Plant Introductions of Watermelon for Resistance to Powdery Mildew" HortScience 40 (1): 154-156 (2005).
Davis "PI 525088-PMR, A Melon Race 1 Powdery Mildew-resistant Watermelon Line" 41(7) 1527-1528 (2006).
Kuzuya "Powdery mildew (*Podosphaera xanthii*) resistance in melon is categorized into two types based on inhibition of the infection processes" 57(9):2093-2100 (2006).
Yousif "Sources of resistance to Watermelon Chlorotic Stunt Virus in melon" Plant Breeding 126; 422-427 (2007).
Leskovar et al., Deficit irrigation influences yield and lycopene content of diploid and triploid watermelon, Acta Hort. 628, ISHS, pp. 147-151 (2003).
Bang et al., Dificit irrigation impact on lycopene, soluble solids, firmness and yield of diploid and triploid watermelon in three distinct environments, Journal of Horticultural Science, 76 (6) 885-890 (2004).
Karchi et al., "Alena" watermelon—a quality cultivar for export and local markets, Hassadeh 61:1284-1285 (1981).
Singh et al., Germination of watermelon seeds at low temperature, Cucurbit Genetics Cooperative Report 24:59-64 (2001).
Showalter, Watermelon color as affected by maturity and storage, Florida Agricultural Experiment Station Journal Series. No. 1179 (1960).

Nerson et al., Harvesting watermelons before ripening impairs their quality, Hassadeh 62:606-607 (1982).
GRIN Accession PI482312 (1983).
Yariv Ben-Naim, The inheritance of resistance against powdery mildew *Sphaerotheca fuliginea* in watermelon *Citrullus lanatus* (Thumb), Master's Degree Thesis; The Mina & Everard Goodman Faculty of Life Sciences, Bar Ilan University, pp. 1-80 (Oct. 2010) plus translation thereof.
Yariv Ben-Naim, The inheritance of resistance against powdery mildew *Sphaerotheca fuliginea* in watermelon *Citrullus lanatus* (Thumb), Master's Degree Thesis; The Mina & Everard Goodman Faculty of Life Sciences, Bar Ilan University, pp. 1-80 (Oct. 2010).
Gürsoy et al.; "In vitro ovule and ovarium culture in watermelon," Cucurbitaceae 2012, Proceedings of the Xth EUCARPIA Meeting on Genetics and Breeding of Cucurbitaceae, Antalya, Turkey, Oct. 15-18, 2012, University of Cukurova, Ziraat Fakultesi, pp. 799-804 (2012) Abstract Only.
Wang & You: "Study on in-vitro culture of mini watermelon," Cucurbitaceae 2012, Proceedings of the Xth EUCARPIA Meeting on Genetics and Breeding of Cucurbitaceae, Antalya, Turkey, Oct. 15-18, 2012, University of Cukurova, Ziraat Fakultesi, pp. 292-298 (2012) Abstract Only.
Kano, Effects of summer day-time temperature on sugar content in several portions of watermelon fruit (*Citrullus lanatus*), J. Hort. Sci. Biotechnol. 79:142-145 (2004).
Ben-Naim, "The inheritance of resistance against powdery mildew *Sphaerotheca fuliginea* in watermelon *Citrullus lanatus* (Thumb)," 156 pages, Oct. 2010, Ramat Gan, Israel.†

\* cited by examiner
† cited by third party

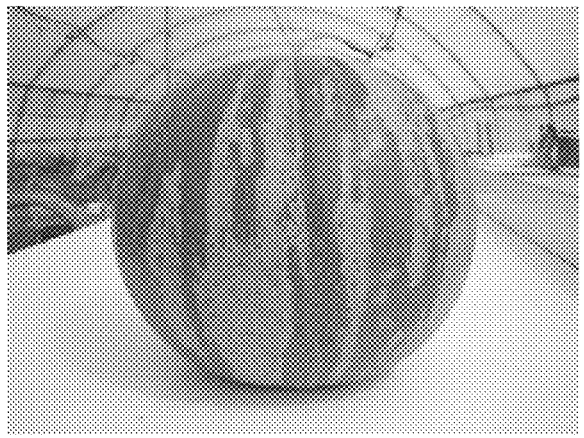
Figure 2A
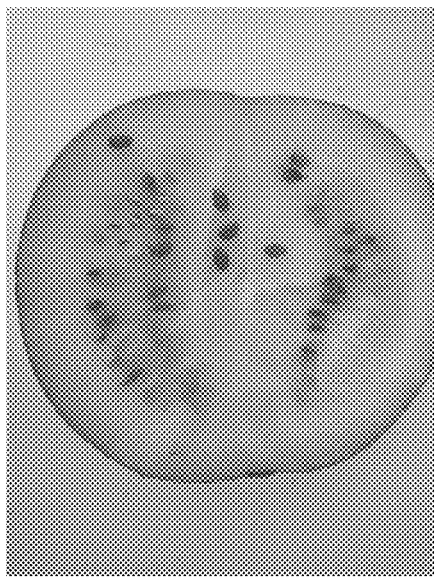
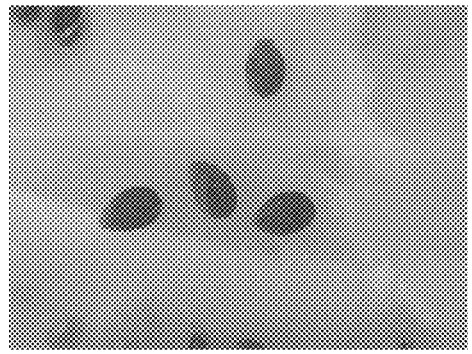
Figure 2C
Figure 2B

WATERMELON PLANTS WITH TOLERANCE TO POWDERY MILDEW

The Sequence Listing in ASCII text file format of 865 bytes in size, created on Nov. 29, 2018, with the file name "2019-01-23SequenceList_VARDI3A," filed in the U.S. Patent and Trademark Office on even date herewith, is hereby incorporated herein by reference.

FIELD OF THE INVENTION

The invention concerns watermelon plants with high tolerance to fungal diseases and to methods for their obtaining.

PRIOR ART

References considered to be relevant as background to the presently disclosed subject matter are listed below:
Davis A R, Tetth A, Whner T, Levi A, Pitrat M, 2006. Watermelon resistance to powdery mildew race 1 and race 2. In G. J. Holmes (ed.) Proc. Cucurbitaceae 2006. Universal Press, Raleigh, N.C.; 412-420.
Levi A, Thomas C E, Trebish T, Salman A, King J, Karalius J, Newman M, Reddy O U K, Xu Y, Zhang X, 2006. An extended linkage map for watermelon based on SRAP, AFLP, SSR, ISSR and RAPD markers. J Amer. Soc. Hort. Sci. 131(3): 393-402
Levi A, Claude E T, 2007. DNA markers from different linkage regions of watermelon genome useful in differentiating among closely related watermelon genotypes. HortScience 42(2): 210-214.
Pitrat M, Besombes D, 2008. Inheritance of *Podosphaera xanthii* resistance in melon line '90625'. Cucurbitacaea 2008, Proceeding of the IXth EUCAPRIA meeting on genetics and breeding of Cucurbitaceae, 135-142.
Robinson R W. Provvidenti R, Shail W, 1975. Inheritance of susceptibility to powdery mildew in the watermelon. The J of Heredity 66: 310-311.
Tetteh A Y, Whener T C, Davis A R, 2010. Identifying resistance to powdery mildew race 2W in the USDA-ARS watermelon germplasm collection. Crop Sci. 50: 933-393.
Zhang H, Gou S, Gong G, Ren Y, 2011. Sources of resistances to race 2WF powdery mildew in US watermelon plant introductions. HortScience, 46(10): 1349-1352.

BACKGROUND OF THE INVENTION

Watermelon (*Citrullus lanatus*), family Cucurbitaceae, is a major cucurbit crop and includes both seeded and seedless fruits.

During the last 50 years, the world production area of watermelon has increased with 62%, from 1.96 million ha in 1961 to 3.16 million ha in 2012. The yield tripled during the same period, resulting in a fivefold total production increase (from 17.8 to 89.0 million tons). The top 10 world watermelon producers include China, accounting for 63% of the production in 2010, followed by Turkey, Iran, Brazil, USA, Egypt, Uzbekistan, Russia, Mexico and Algeria. In the United States, watermelon is major vegetable crop. Major production states are Florida, California, Arizona, Texas and Georgia. In 2005, the total production of watermelon in the United States was 1.7 million Kg, with a farm value of 410$ million.

The watermelon fruits have varying size ranging from very big watermelon, at times >7 Kg to medium, 4-7 kg and small watermelons (<4 kg, known as the mini or personal size). The red pigment in red—fleshed watermelon is from the carotenoid lycopene and comprises 70-90% of the total carotenoids in watermelon.

In recent years watermelon has been characterized also at the DNA level and DNA markers from different linkage regions of the watermelon genome have been identified using various PCR reaction techniques [Levi A et al., 2006, Levi A et al., 2007].

Powdery mildew (PM) is one of the most common diseases of watermelons. In the last years, the PM disease spread worldwide and become a significant threat [Zhang et al., 2011]. Two species *Podosphaera xanthii* (formerly *Sphaerotheca fulginea*) and *Golovinomyces cichoracearum* (formerly *Erysiphe cichoraearum*), can induce worldwide typical and identical symptoms [Pitrat & Besombes, 2008].

The PM disease is spread both in open fields and in greenhouses. In open fields the disease is usually limited to dry areas or to dry seasons.

The first appearance of the disease is being recognized as white colony, 2-3 mm diameter, appearing on the cotyledons or on the leaves. With time, the colonies grow, unite and create continues cover of white mycelium and white spores on both sides of the leaves, which looks like powder. Spores number can reach up to 50-100,000 per 1 $cm^2$.

Later colonies may appear on the stems and even on the fruits. Necrosis starts a week after the infection, depends on environment conditions. Under optimal growth conditions of the pathogen and without a suitable treatment, the fungus can cause death of the whole plant in a couple of weeks. The spores' germination process occurs in drought conditions. Presence of water on the tissue prevents the germination. The optimal temperature for germination is 20° C.-23° C. (minimum 5° C., maximum 35° C.). Intensive photosynthesis improves the germination.

Watermelons were resistant to older races of *Sphaerotheca fuliginea* present in the U.S. in the 1970s. However, in recent years, a single recessive gene pm having high susceptibility to PM was found in the Plant Introduction, PI 269677 [Robinson et al., 1975].

Currently, two races of PM are found in the U.S. named race one (PM1W) and race two (PM2W), and induce a susceptible reaction in most cultivars. In the past, watermelon was considered to be free of powdery mildew. In recent years, powdery mildew outbreaks have been reported (also) in the United States. The disease has been confirmed in South Carolina, Georgia, Florida, Maryland, Texas, Oklahoma, Arizona, New York and Carolina. 1654 *Citrullus* cultigens from the U.S. plant introduction collection were evaluated for resistance to PMW2. 93% of the cultigens had total plant disease severity rating of >4.0 (sensitive), which means at least 20% mycelium coverage on leaves and stems. 7% of the cultigens had high resistance (≤0.0) or intermediate resistance (3.1-4) [Tetteh et al., 2010, Davis et al., 2006].

PM1W usually appears at the beginning of a season where the plant is still considered a young plant, while PM2W usually appears late in the season, after fruit setting.

The major damages of PM on watermelon are decrease in the yield quality, namely decreased fruit size and number of fruits per plant. The fruits which remain have poor fruit quality and poor flavor and experience short storage life.

It has been previously reported that PM can be controlled with fungicides. However, resistance to the recommended fungicides, especially the strobilurins and myclobutanil was reported. Also the disease control often requires the use of systemic fungicide because spray application to the underside of leaves is difficult. Currently, effective control of powdery mildew is achieved with alternating preventative applications of mancozeb with azoxystrobin [Tetteh et al., 2010].

Therefore, there is a need for an effective and safe method to control PM while minimizing the use of chemicals.

SUMMARY OF DISCLOSURE

The present disclosure provides, in accordance with a first of its aspects, a triploid hybrid watermelon (*Citrullus lanatus*) plant characterized by tolerance to powdery mildew (PM) and capable of producing seedless fruits with a total soluble solid in the range of 10% to 13%, and a red fruit flesh color.

In accordance with a second of its aspects, the present disclosure provides seeds of a triploid watermelon plant characterized by tolerance to powdery mildew (PM) and capable of producing seedless fruits with a total soluble solid in the range of 10 to 13%, and a red fruit flesh color.

Further, there is provided by a third aspect of the present disclosure a diploid watermelon line having at least tolerance, at time at least intermediate resistance to PM and being capable of pollinating a tetraploid watermelon to produce a triploid hybrid watermelon with tolerance to powdery mildew (PM) and capable of producing seedless fruits with a total soluble solid in the range of 10% to 13%, and a red fruit flesh color, as disclosed herein.

In accordance with further aspects of the present disclosure there are provided pollen and seeds of the diploid watermelon line disclosed herein.

In accordance with another aspect of the present disclosure there is provided a method of producing a triploid hybrid watermelon plant characterized by tolerance to powdery mildew (PM) and capable of producing seedless fruits with a total soluble solid in the range of 10% to 14%, at times in the range of 11% to 13.5%, and a red fruit flesh color, the method comprising:
  a. planting a PM sensitive female parent tetraploid watermelon line having a total soluble solids of at least 10%, essentially red fruit flesh color, flesh firmness of between 60 to 80 and thousand seeds weight (TSW) of between 25 to 90 g;
  b. pollinating said tetraploid watermelon line with pollen from a male parent diploid watermelon line having at least tolerance to PM;
  c. planting said triploid watermelon seeds to produce said triploid watermelon plants.

Further provided herein is a method of producing a triploid hybrid watermelon fruit harvested from a plant with tolerance to powdery mildew (PM) and the fruit being seedless, with a total soluble solid in the range of 10% to 14%, at times within the range of 11% to 13.5% and at times about 13.5%, and a red fruit flesh color and, the method comprising:
  a. planting a PM sensitive female parent tetraploid watermelon line having a total soluble solid of at least 10%, red fruit flesh color, flesh firmness of between 60 to 80 and TSW of between 25 to 90 g;
  b. pollinating said female tetraploid watermelon line with pollen from a male parent diploid watermelon line having at least tolerance to PM;
  c. planting said triploid watermelon seeds to produce said triploid watermelon hybrid plants and exposing said triploid hybrid plant to a pollinizer to produce said triploid seedless watermelon fruit;
  d. harvesting triploid seedless watermelon fruits from said triploid hybrid watermelon plants.

In some embodiments, the diploid watermelon male parent is one identifiable by a marker locus which co-segregates with PM tolerance trait, the marker locus being identified by a PCR reaction comprising amplification of a DNA fragment with a pair of PCR oligonucleotide primers represented by a forward primer 5' to 3' of SEQ ID NO:1 (TGAGTC-CAAACCGGATA, also known as mel) and a reverse primer 5' to 3' of SEQ ID NO:2 (GACTGCGTACGAATTAAT also known as eml) or any other marker located on same chromosome that is statistically correlated and genetically linked to the PM tolerance trait.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2A-2D are images of the wild type PM resistant watermelon PI 482312 showing the fruits striped rind (FIG. 2A), yellow flesh (FIG. 2B), green seeds (FIG. 2C) and PM tolerant leaves (FIG. 2D).

DETAILED DESCRIPTION OF EMBODIMENTS

Generally, the present disclosure is based on the unique development of a triploid hybrid watermelon plant lines with agriculturally acceptable tolerance to powdery mildew and capable of producing edible seedless fruits. These triploid hybrid watermelon plant lines are the subject of the first aspect of the present disclosure.

By a second aspect, there are provided diploid male inbred watermelon lines with at least tolerance, at times at least intermediate resistance to PM and tetraploid female inbred watermelon lines having red flesh color and total soluble solids of at least 10%, which when crossed, provide the triploid watermelon lines capable of producing seedless fruits with a TSS in the range of 10% to 14%, at times in the range of 11% to 13.5%.

Also provided herein are methods of use of the watermelon lines, as further discussed below.

In the present the following terms are to be understood as having the following meaning:

Powdery mildew (PM)—In the context of the present disclosure when referring to Powdery mildew (PM) it is to be understood as having the meaning known in the art, i.e. a fungal disease characterized by spots or patches of white to grayish, talcum-powder-like growth. As appreciated, different types of PM are differentiated using various melon differentials. When referring to watermelon, PM refers to sensitivity of a watermelon plant to at least one of PM race 1 and race 2 (hereinafter "PMW1", and "PMW2", respectively).

Figure 1A:
FIG. 1A-1D are images of PM sensitive watermelon plant infected with white mycelium spores appearing on the leaves (FIG. 1A); on the stems (FIG. 1B) and even on the fruits (FIG. 1C); which may result in death of the whole plant in a couple of weeks (FIG. 1D).
Figure 1B:
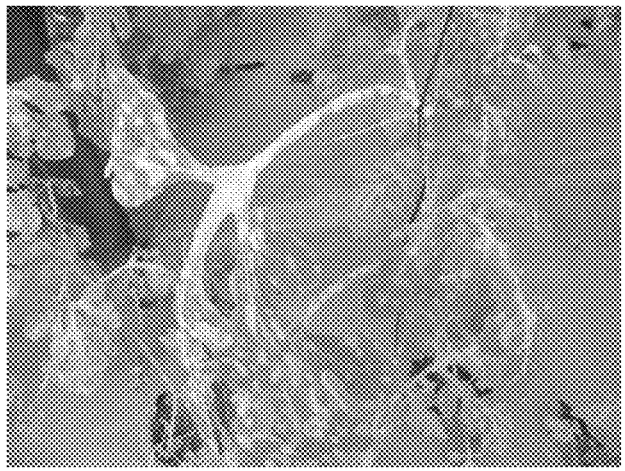
Figure 1C:
Figure 1D:

The sensitivity of a plant is determined according to the size of mycelium and time of its appearance on the plant during the cultivation period. Typically, the first appearance of the disease is recognized as white colony, 2-3 mm diameter, appearing on the cotyledons or on the leaves. With time, the colonies grow, unite and create continues cover of white mycelium and white spores on both sides of the leaves, which looks like powder. FIG. 1A shows leaves of a PM sensitive watermelon infected with white mycelium spores. Spores number can reach up to 50-100,000 per 1 $cm^2$. Later colonies may appear on the stems (FIG. 1B) and even on the fruits (FIG. 1C). Necrosis starts a week after the infection, depending on environment conditions. Under optimal growth conditions of the pathogen and without a suitable treatment, the fungus can cause death of the whole plant in a couple of weeks (FIG. 1D). The spores germination process occurs in drought conditions. Presence of water on the tissue prevents the germination. The optimal temperature for germination is 20-23° C. (minimum 5° C., maximum 35° C.). Intensive photosynthesis improves the germination.

Figure 1E:
FIG. 1E is an image of PM tolerant diploid male plants (left) and PM sensitive diploids male plants (right), growing in a greenhouse in southern of Israel. The plants were grown in greenhouse and were inoculated by spreading uniformly the fungus by hand in the greenhouse. Also, the plants in the greenhouse were not treated with fungicides.

Tolerance or resistance—tolerance (or lack of sensitivity) is ranked between 1 to 9, with 1 defines a high degree of sensitivity (no tolerance) that even results in necrosis, and 9 defining high tolerance or even up to resistance. Thus, it is be understood that a sensitive plant has low tolerance to PM and lack of sensitivity is indicative of tolerance or resistance to PM. Accordingly, a plant ranked between 6-7 is regarded as tolerant, a plant ranked 7-8 is regarded high tolerance or intermediate resistance, and a plant ranked 8-9 is regarded as resistant. In some embodiments, when referring to tolerance, intermediate resistance or resistance, it is to be understood as referring to a plant comprising a tolerance locus being linked to a genetic background or genetic determinant obtainable from the genome of a wild type watermelon plant being agriculturally recognized as having resistance to PM (scale of resistance above 7, and preferably above 8), such as the PM watermelon plant designated according to the plant index PI 482312 [Tetteh et al. 2010]. A comparison between PM sensitive line (ranked as 2) and PM tolerant line (ranked as 8) can be seen in FIG. 1E (on the left is the PM tolerant and on the right is the sensitive line).

Seedless—In the context of the present disclosure it is to be understood that a seedless plant is defined by lack of mature seeds in its fruit and thus lacking the capacity to propagate via seeds. It is to be understood that a seedless fruit may include seed coats and with respect to the present invention a seedless fruit is one comprising between 0-200 seed coats.

Fruit shape—Generally, a watermelon fruit may have a flat, round, oval and elongated shape. The shape may be defined by the ratio between the major and minor axes of the fruit, such that an oval shape is defined by a ratio between the major axis 1.2-1.4 to the minor axis 1 as a ratio between 1.2:1 to 1.4:1 while in an elongated fruit the ratio is define between 1.5:1 and 1.8:1. Equally the shape may be scaled between 10 to 90, with 10 representing a flat fruit, 50 round fruit, 60-70 represents an oval fruit and 75-90 represents an elongated fruit. This scale is calculated based on the fruit's measurements ratio (length/width)×50 (a round fruit).

Fruit regularity—may be ranked between 10 to 90, where 10 indicates an irregular shape and 90 indicates that the fruit is regular in shape.

Vigor—watermelon plants may be characterized by their overall condition or their "vigor", the vigor being scaled between 10 to 90; 10 defining a weak vigor and 90 defining a very strong vigor. Vigor is determined based on plant size and leaf blade size.

Flowering period—flowering period, also understood as earliness of a plant defined by the time from planting to the first female flower and time from flowering to fruit maturation. In accordance with the present disclosure, earliness, i.e. the female flowering time is scaled between 10 to 90; 10 defining a very early female flowering time and 90 defining a very late female flowering time. In the summer, time to early (10) female flowering is defined between 20-25 days after planting and late (90) is defined 40-45 days after planting.

Fruit setting—the occurrence of fruits setting in a plant, and in the context of the present disclosure, the setting is scaled between 10 to 90; 10 reflecting very few up to 0.5 fruit per plant and 90 reflecting a large fruits number per plant (above 4).

Flower sex—flower may be monoecious (M), namely, a watermelon plant species in which male and female organs are found on the same plant but in different flowers, hermaphrodite (H), namely, a plant where the male and female organs are present on the same flower; and andromonoecious (AM), namely, a plant that has both hermaphrodite and male flowers.

Rind color—the color of the rind of the fruit may be from smooth gray, to striped fruit like brake green stripe (citron type), thin stripes (Jubilee/Tiger type), dark medium stripes (crimson type) and dark wide stripes on light green background (All sweet type) to smooth light or dark green rind.

Number of fruit per plant—the number of fruit per plant is well appreciated parameters in determining quality of a plant.

Striping—watermelons may be distinguished by the appearance of stripes on the outer surface of the rind. The stripes may cover small portions of the fruit's rind, medium coverage and also may cover the majority of the fruit's rind. The stripes may be very thin, medium or very thick. Thus, the overall stripes coverage of the rind, may be defined by percentage, with low coverage being regarded as less or equal to 10% rind cover, medium coverage—50% cover, and high/thick coverage—70-80% rind cover and very high/thick coverage—90% rind cover. The stripes are typically green stripes.

Weight—watermelon fruits are typically characterized by their weight. Small fruits are those typically weighting less than 4.0 kg, at times, between 1.5 and 4.0 kg and at times, between 2-4 Kg, and are recognized as the mini or personal sized watermelons, and large fruits are those typically weighting between at least 4.0 Kg. The group of large fruits may be further divided into two sub groups of sizes 4. Kg-6 Kg (also referred to as midi sized fruits) and at least 7 Kg. Thus, in the context of the present disclosure, the fruits may be mini, having a weight of less than 4.0 kg, between 2.0 and 4.0, midi, having a weight of between 4.0 and 6 kg, and large fruits having a weight larger than 7 kg, such as between 7-14 kg or 7 kg to 10 kg.

Flesh color—generally, watermelon flesh color may vary from scarlet red (dark red), coral red (light red), orange, salmon yellow, canary yellow, or white. In the context of the present disclosure, when referring to red it is to be understood to cover also shades or hues of red, including dark red or red like color. The flesh color may be determined using Pantone Color scale and in accordance with some embodiments, the red color is identified by any one of the Pantone color scale including "red" in their name as available on line at www.pantone.com (2012). In some embodiments, the flesh color is dark red.

Flesh firmness—flesh firmness defines the force necessary to break the flesh tissue at ripening. Firmness of the watermelon plants disclosed herein was measured by PENETROMETER FRUIT PRESSURE TESTER mod. FT 011 (0-11 lbs.), IRC. It measures the pressure necessary to force a plunger of specified size into the pulp of the fruit. Such pressure is measured in pounds or Kilograms. The scale in accordance with the present disclosure was ranked between 10 to 90 (50 being 21b5), where 10 indicates that the flesh is very soft (e.g. penetrometer scale below 2), and 90 indicates a very firm flesh (e.g. penetrometer scale above 4). Penetrometer scale between 3-3.5 is considered firm flesh.

Rind thickness—is usually measured in millimeters from the outer edge of the fruit to the boundary between the white mesocarp and colored endocarp. The thickness may vary from very thick, e.g. >19 mm, medium thickness 10-19 mm, to low thickness <10 mm.

Rind crack—rind crack defines the tendency of the watermelon rind to crack by itself and in accordance with the present disclosure, rind cracks are ranked from 10 to 90, where 10 defines a strong, uneasily cracked rind (no tendency to crack at all) and 90 defines an easily cracked rind (the fruit is cracking by itself in the field).

Taste—while being somewhat a subjective characteristic, a fruit of a watermelon may vary from tasteful, tasteless, bitter etc.

TSS (Total Soluble Solids)—is a measure of the percent soluble solids (TSS) in a sample of a plant juice, used as an index/parameter for sugar quantity in the fruit (sweetness). The TSS was measured by ATAGO refractometer (atago.net/USA/products_hsr.php), Brix 0.0 to 33.0%, Automatic Temperature Compensation, The refractometer designed to measure the refractive index of the solution. The Brix percentage represents the total concentration of total soluble solids (TSS) in the sample.

Deposit—deposit of representative seeds of the lines referred to by the Applicant's internal reference and having representative seeds deposited on 24 Aug. 2012, at the NCIMB recognized institute for purposes of patent procedure and according to which the following Accession number for the deposition of *Citrullus Lanatus* was provided NCIMB 42044 (internal reference S12-12.701), as well as the one deposited on Oct. 14, 2013, and having representative seeds deposited under Accession No NCIMB 42172 (internal reference 12.704bPMI-W12), as well as those deposited in the same NCIMB institute on Feb. 16, 2015, referred to by Applicant's internal references 12.702b-W14 and 12.135b-W14 and having, respectively, the Accession Nos. NCIMB 42359 NCIMB 42360. The full name and address of the NCIMB institute is NCIMB Ltd., Ferguson Building, Craibstone Estate, Bucksburn, Aberdeen, AB21 9YA, Scotland.

Turning now to the present disclosure, there is provided, in accordance with a first aspect, a triploid watermelon hybrid plant characterized by tolerance to powdery mildew (PM) and capable of producing seedless fruits with a total soluble solid (TSS) in the range of 10% to 14%, at times 11% to 13.5% and red fruit flesh color.

In accordance with some embodiments, the triploid hybrid watermelon plant has a tolerance rank of at least 6, preferably, at least 7, at times, between 7 to 9, to at least one strain of PM, at times, to at least PMW1 or PMW2 and yet at times, to PMW1 and PMW2.

When referring to various characteristics of watermelon plants, it is noted that the triploid hybrid watermelon plant disclosed herein may be further characterized by any one or more of the following.

In some embodiments, the triploid hybrid watermelon plant is characterized by vigor of between 50 to 80, at times about 70 (in the scale between 10 to 90).

In some embodiments, the triploid hybrid watermelon plant is characterized by earliness of between 30 to 70, at times between 40 and 60.

In some embodiments, the triploid hybrid watermelon plant is characterized by fruit setting of between 20 to 50.

In some embodiments, the triploid hybrid watermelon plant is characterized by flower sex being monoecious (M), namely, a triploid watermelon plant species in which male and female organs are found on the same plant but in different flowers.

In some embodiments, the triploid hybrid watermelon plant is characterized by rind color of crimson to dark crimson color. In some other embodiments, the plant is characterized by tiger type rind.

In some embodiments, the triploid hybrid watermelon plant is characterized by green stripes on the fruit, and in some embodiments, gray fruit having thick dark green stripes that cover between 60% to 90%, typically about 80% of the fruit.

In some embodiments, the triploid hybrid watermelon plant is characterized by number of fruits per plant in the range of 1 to 4, preferably 2-3.

In some embodiments, the triploid hybrid watermelon plant is characterized by flesh color being scarlet red (dark red) to coral red (light red) according to PANTONE scale color: http://www.pantone.com/pages/pantone/colorfinder.aspx. Dark red (Pantone 18-1664 TCX Fiery Red), light red (Pantone Red 032 C). In some embodiments, the flesh color is dark red. In some other embodiments, the flesh color is light red.

In some embodiments, the triploid hybrid watermelon plant is characterized by flesh firmness between 60 to 80, at times about 70.

In some embodiments, the triploid hybrid watermelon plant is characterized by rind crack of between 10 to 90, typically about 10 to 30, i.e. no or very little (insignificant) tendency to crack.

In some embodiments, the triploid hybrid watermelon plant is characterized by good taste, as determined by a human subject tasting the fruit as being non-bitter.

In some embodiments, the triploid hybrid watermelon plant is characterized by TSS (Brix %) between 10% to 14%, at times between 11% to 13.5% or about 13.5%.

In some embodiments, the triploid hybrid watermelon plant is characterized by tolerance to at least PMW1R, at times to at least one of PMW1R and PMW2R.

In some embodiments, the fruit is an essentially round fruit. In some other embodiments, the fruit is oval. The fruit is not regarded as an elongated fruit, i.e. the fruit is scaled between 50 to 70 but not above 70 (which indicative, as described above, of an oval fruit shape).

In some embodiments, the fruit is a mini fruit, having a weight in the range of 2-4.0 kg, preferably between 2.5-3.5 kg or 2.8 kg-3.2 kg and in some other embodiments the fruit is a midi fruit, having a weight between 4 to 6 kg, at times, between 4-5 kg.

In some embodiments the fruit is round and has a weight in the range of 2-4.0 kg, preferably between 2.8-3.2 Kg.

In some embodiments the fruit is oval and has a weight greater than 4.0 kg, at times, between 4 to 6 kg, or even between 6 to 10 kg.

The triploid hybrid watermelon plant disclosed herein carries genetic background from the PM watermelon plant designated according to the plant index PI 482312 [Tetteh et al. 2010] as having tolerance equivalent to tolerance of rank 6 according to the tolerance scale of the present disclosure, or 3.5 according to Tetteh et al., 2010 Comparison between currently used ranking (Numerical Rank/Current) and ranking according to Tetteh et al., 2010 is provided below, with "R" representing Resistant (rank 8-9), "IR" representing Intermediate Resistant or, as used in the present disclosure, Tolerance; and "S" representing susceptibility or sensitivity.

| Numerical | 0 | 1 | 2 | 3 | 4 | 5 | 6 | 7 | 8 | 9 |
|---|---|---|---|---|---|---|---|---|---|---|
| Current | — | S | S | S | S | S | IR | IR | R | R |
| Tetteh et al. 2010 | R | R | R | R* | IR | S | S | S | S | S |

*≤3 represents "R", 3.1 << 4 represent "IR" (Tetteh et al., 2010)

The winter 2011 offspring (referred to herein as W11-701-1 or PI 482312) were originally obtained from self-pollination of this PI from summer 2005.

When referring to "genetic background" in the context of the present invention it is to be understood to refer to a cultivated watermelon plant as disclosed herein (the diploid or the triploid plant) containing a genome comprising at least a qualitative trait locus (QTL) which contributes to PM tolerance. In some embodiments, the QTL is genetically linked to at least one marker locus that co-segregates with the PM tolerance trait and can be identified by a PCR oligonucleotide primer or a pair of PCR oligonucleotide primers being represented by a forward primer of SEQ ID NO:1 and a reverse primer of SEQ ID NO:2.

The identification of a marker locus identifiable by the pair of PCR oligonucleotide primers represented by the forward primer of SEQ ID NO:1 and the reverse primer of SEQ ID NO:2 is based on System Related Amplified Polymorphism (SRAP) molecular marker system making use of a series of publically available primer pairs for which at least one marker locus of 480 bp has been identified in the genome of all the diploid male seed samples analyzed but was missing from the genome of the female tetraploid.

Specifically, as will be further discussed below, various combinations of the watermelon forward primer sequence identified the commercial name me1 (SEQ ID NO:1), me2, me3, and the reverse primer sequence identified by the commercial name em1 (SEQ ID NO:2), em2, em3, em4 and em5 were used as primer pairs and the combination of me1em1 was positive for a marker locus of 480 bp.

In some embodiment, the genetic background is to be understood as meaning that the allele at the QTL in the cultivated triploid hybrid watermelon genome contributing to the said tolerance is obtainable from a plant having the genetic background of at least one of PI 482312 or at least one of the cultivated diploid watermelon lines identified herein as PI48312, 572 (W11-768-B), or identified herein as 573-r-1-2 (PMS12-378-2) or of a progeny or an ancestor of any of these PM tolerant watermelon plants comprising said qualitative trait locus.

Thus, in accordance with the present disclosure there is also provided a triploid hybrid watermelon plant, comprising a tolerance locus is genetically linked to at least one marker locus which co-segregates with PM tolerance trait and comprises a marker that can be identified in a PCR reaction by amplification of a DNA fragment with a pair of PCR oligonucleotide primers represented by a forward primer of SEQ ID NO:1 and a reverse primer of SEQ ID NO:2 or any other marker located on same chromosome that is statistically correlated and genetically linked to the PM tolerance trait.

In some embodiments, the marker locus comprises about 480 base pairs.

In some embodiments, the triploid hybrid watermelon plant disclosed herein is produced by crossing a tetraploid female watermelon with a male plant being a PM tolerant diploid line.

In some embodiments, the male plant selected from the group consisting of lines designated herein W11-701-1; 539 (S09-539-1); 554-F4 (W09-F4-568-1); 554-F5 (BD10-F5-151-13); 554-F7 (S11-F7-548-1); 572 (W11-768-B), and 573-r-1-2 (PMS12-378-2).

The present disclosure also concerns seeds of a triploid watermelon plant that produces a watermelon plant characterized by tolerance to powdery mildew (PM) and capable of producing seedless fruits with a total soluble solid in the range of 10% to 14%, at times, 11%-13.5% and a red or red-like fruit flesh color.

In some embodiments, the seeds of a triploid watermelon plants are a line designated S12-12.701 having representative seeds deposited on Aug. 24, 2012 under Accession No. NCIMB 42044 In some other embodiments, the seeds of a triploid watermelon plants are a line designated 12.704bPMI-W12 and having representative seeds deposited on Oct. 14, 2013, under Accession No. NCIMB 42172. In yet some other embodiments, the seeds of a triploid watermelon plants are a line designated 12.702b-W14 having representative seeds deposited under Accession No. NCIMB42359. In yet a further embodiment, the seeds of a triploid watermelon plants are a line designated 12.135b-W14 having representative seeds deposited under Accession No. NCIMB42360.

In some embodiments, the seeds of the triploid watermelon plant as disclosed herein are selected as one comprising a tolerance locus that is genetically linked to at least one marker locus which co-segregates with PM tolerance trait and comprises a marker that can be identified in a PCR reaction by amplification of a DNA fragment with a pair of PCR oligonucleotide primers represented by a forward primer of SEQ ID NO:1 and a reverse primer of SEQ ID NO:2.

Yet, the present disclosure also provides any progeny of a triploid watermelon line disclosed herein. In some embodiments, the progeny has the genetic background of the triploid disclosed herein. In some embodiments, the genetic background is of at least one of the watermelon plants having representative seeds deposited under one of Accession No. NCIMB 42044, NCIMB 42172, NCIMB42359 and NCIMB42360. In yet some other embodiments, the genetic background of the triploid is exhibited in the progeny by at least PM tolerance or by the existence of at least one QTL which contributes to the PM tolerance, or comprises a tolerance locus that is genetically linked to at least one marker locus which co-segregates with PM tolerance trait and comprises a marker that can be identified in a PCR reaction by amplification of a DNA fragment with a pair of PCR oligonucleotide primers represented by a forward primer of SEQ ID NO:1 and a reverse primer of SEQ ID NO:2.

The reproduction of triploid progenies may be by any technique known in the art, including, without being limited thereto, cutting, tissue culture, embryo rescue, chromosome doubling, double haploids and mutations. Some methods are described by Wang & You: Study on in-vitro culture of mini watermelon, in Cucurbitaceae, 2012 p. 292-298; Gürsoy et al; In vitro ovule and ovarium culture in watermelon, in Cucurbitaceae, 2012 p. 799-804. Wang & You, 2012 and Gürsoy et al., 2012 in Cucurbitaceae, 2012]

The present disclosure also provides any seedless watermelon fruit of the triploid watermelon line disclosed herein, the seedless watermelon fruit having at least tolerance to powdery mildew (PM) and one or more of a total soluble solid (TSS) in the range of 10% to 14%; preferably 11%-13.5% and a red fruit flesh color.

In some embodiments, the genome of the seedless watermelon fruit of the triploid watermelon line is characterized by genetic background of its male parent having tolerance to resistance to PM.

In some embodiments, the triploid provides a mini fruit with a fruit size in the range of 2 to 4.2 kg. The fruit is typically round.

In some embodiments, the mini fruit are the harvest of a triploid watermelon having representative seeds deposited under the Accession No. NCIMB 42044 and/or NCIMB42172 and/or NCIMB42359.

In some other embodiments, the triploid provides a fruit size greater than 4.5 kg, at times greater than 7 kg. The fruit is typically oval.

In some embodiments, the large fruit are the harvest of a triploid watermelon having representative seeds deposited under the Accession No. NCIMB42360.

In another aspect, the present disclosure provides a diploid watermelon line having tolerance to PM and being capable of pollinating a tetraploid watermelon to produce a triploid hybrid watermelon as disclosed herein.

In general, triploid hybrid watermelon plants are created by crossing a tetraploid female parent line with a diploid male parent line. The tetraploid female parent line and the diploid male parent line are typically planted in a field or greenhouse and the female tetraploid flower is pollinated as known in the art. The triploid seeds that are produced in the fruit of the tetraploid plants are planted in a field with a diploid pollinizer plants to produce fruits that are seedless.

In some embodiments, the diploid watermelon line has a genetic background of the watermelon identified as P1482312. The winter 2011 offspring obtained from self pollination being referred to herein as W11-701-1, at least with respect to the trait of tolerance to PM, as well as any diploid PM tolerant plant selected from the lines designated herein 572 (W11-768-B), or designated 573-r-1-2 (PMS12-378-2).

In some embodiments, the diploid watermelon line disclosed herein may be characterized by lines referred to herein as 539 (S09-539-1), 554-F5 (BD10-F5-151-13) and 554-F7 (S11-F7-548-1) all having the genetic background of at least one of the disclosed and deposited male parent diploid plant, and/or at least comprising a tolerance locus being linked to a genetic background or genetic determinant obtainable from the genome of a wild watermelon plant having resistance to PM, such as the PM watermelon plant designated according to the plant index PI 482312 or of the cultivated and herein deposited diploid watermelon plants.

In some embodiments, the diploid watermelon line disclosed herein has tolerance to one or both of PMW1 and PMW2.

In accordance with this aspect, there is also provided pollen of a diploid watermelon line disclosed herein.

Yet further disclosed herein are the seeds of the said diploid watermelon line as well as any other form for obtaining progeny of the diploid watermelon. Thus in the context of the present disclosure, when referring to diploid watermelon line having tolerance to one or both of PMW1 and PMW2 it is to be understood as encompassing also any sexually or asexually reproduced progeny of the above recited diploid male watermelon plant lines.

The diploid watermelon line disclosed herein may be further characterized independently by any one of the following parameters. Therefore, while being presented herein as a list, each parameter below constitutes an independent embodiment of the present disclosure and may be combined with one or more other parameter from this list:

vigor of between 60 and 90, typically about 70;
earliness of between 25 and 50, typically about 30-40;
flower setting of between 30 to 50, at times 30-40;
flower sex being monoecious (M).
rind color of tiger (narrow stripes) or gray or crimson (wide dark stripes); preferably gray.
number of fruits per plant in the range of 2 to 4.
fruit regularity in the range of 60 to 80;
fruit weight of between 2 to 12 kg.
flesh color being red to deep/dark red.
flesh firmness between 60 to 80, typically about 70.
rind thickness between 9 mm to 11 mm, typically about 10 mm
rind crack of between 10 to 80, typically about 10.
seed color being brown or black.
weight of a 1,000 seeds being between 20 to 65.
seed size of between 4-6×6-11 mm.
TSS of at least 10%, at times between 10% and 13%;
PMW1 and PMW2 tolerance in the range of 7-8 (also referred to as intermediate resistance).

In accordance with another aspect, the present disclosure also provides a tetraploid female watermelon selected from the line designated W11-F99-448-B1, including any sexually or asexually produced progeny thereof having a flesh color selected from red, dark red or red like, and TS S of at least 10%.

To create tetraploid female watermelon line, it is known in the art to use chemicals that affect mitotic processes of a diploid inbred line so as to affect the number of chromosomes that are eventually obtained. The best known chemical is colchicine. Oryzaline, ethalfluralin and dinitroanilines have also been used for doubling of existing chromosome content.

The diploid line used to create a tetraploid is selected based on the desired traits for the tetraploid line. Methods for developing tetraploid plants are described in the art [Kihara H. 1951, triploid watermelons. *Processings of American Society of Horticultural Science* 58:217-230; Eigstri O. J., 1971 *Seedless Triploids. HortScience* 6:1-2; Donald N. Maynard, Watermelons, characteristics, Production and Marketing, pp. 63-67, 2001]

Cross pollination between a tetraploid line, the female parental line, and a diploid line, the male parental line, are accomplished by either hand or insects (mostly bees) pollination. In bee pollination all the male flowers covered by capsules and the female flowers are open pollinated by bees. In hand pollination Male flowers of the diploid male parent line are collected in the early morning before the visit of insects and female flower buds are uncovered where pollination with the collected fresh male flowers is performed, e.g. by hand.

The tetraploid watermelon plant may be characterized by one or more of the following parameters. Therefore, while being presented herein as a list, each parameter below constitutes an independent embodiment of the present disclosure and may be combined with one or more other parameter from this list:

vigor of between 40 and 70;
earliness of between 50 and 70;
flower setting of between 50 to 70;
flower sex being monoecious (M).
rind color crimson (wide dark stripes) or tiger (narrow dark stripes) or gray, preferably crimson;
number of fruits per plant in the range of 2 to 4.
fruit regularity in the range of 60 to 80;
fruit weight of between 2 to 8.5 kg.
flesh color being red to deep/dark red.
flesh firmness between 60 to 80, typically about 70.
rind thickness between 12 mm to 16 mm.
rind crack of between 10 to 80, typically about 10.
seed color being brown or black.
weight of a 1,000 seeds (TSW) being between 25 g. to 90 g.
seed size of between 4-7×7-12 mm.
TSS of at least 10%, at times between 10% and 13%
PMW1 and PMW2 sensitive (in average scaled 2).

In yet a further aspect, there is provided by the present disclosure a method of producing a triploid hybrid watermelon plant characterized by tolerance to powdery mildew (PM) and capable of producing seedless fruits with a total soluble solid (TSS) in the range of 10% to 14%, and a red fruit flesh color, the method comprising:

a. planting a field with a PM sensitive female parent tetraploid watermelon line having a total soluble solid of at least 10%, and red fruit flesh color, flesh firmness of between 60 to 80 and TSW of between 25 g. and 90 g.

b. pollinating said tetraploid watermelon line with pollen from a male watermelon line having tolerance to PM, to produce triploid watermelon seeds;

c. planting said triploid watermelon seeds to produce said triploid watermelon plants having tolerance to PM.

Further provided is a method of producing a triploid hybrid watermelon fruit harvested from a triploid watermelon plant with tolerance to powdery mildew (PM) and the fruit being seedless, and with a total soluble solid in the range of 10% to 14%, preferably in the range of 11% to 13.5% or about 13.5%, and red fruit flesh color, the method comprising:

a. planting a PM sensitive female parent tetraploid watermelon line having a total soluble solid of at least 10%, red or red-like fruit flesh color, flesh firmness of 80 and TSW of between 25 g. to 90 g.

b. pollinating said tetraploid watermelon line with pollen from a male parent diploid watermelon line having tolerance to PM, to produce triploid watermelon seeds;

c. planting said triploid hybrid watermelon seeds and exposing the triploid hybrid plant to a pollinizer to produce said triploid watermelon plants with seedless fruits.

d. harvesting triploid seedless watermelon fruit from said triploid hybrid watermelon plants.

In some embodiments, the male watermelon is selected from the group consisting of lines designated 539 (S09-539-1); 554-F4 (W09-F4-568-1); 554-F5 (BD10-F5-151-13); 554-F7 (S11-F7-548-1), 572 (W11-768-B), and 573-r-1-2 (PMS12-378-2).

In some embodiments, the male parent diploid watermelon line is selected by identifying a marker locus which co-segregates with PM tolerance trait using, said identification comprises a PCR reaction comprising amplification of a DNA fragment with a pair of PCR oligonucleotide primers represented by a forward primer of SEQ ID NO:1 and a reverse primer of SEQ ID NO:2 or any other marker located on same chromosome that is statistically correlated and genetically linked to the PM tolerance trait.

In some embodiments, the male diploid is identified when said marker comprises or has about 480 base pairs.

In some embodiments, planting is of only triploid watermelon seeds having a genetic background of the selected male parent.

In some embodiments, the planting is of seeds that their genetic background comprises a marker locus identifiable by a PCR reaction comprising amplification of a DNA fragment with a pair of PCR oligonucleotide primers represented by a forward primer of SEQ ID NO:1 and a reverse primer of SEQ ID NO:2.

In some embodiments, the method comprises selecting triploid watermelon seeds comprising in their genome a PM tolerance locus that is genetically linked to at least one marker locus which co-segregates with the PM tolerance trait, said selection comprises identifying said marker with a PCR amplification reaction of a DNA fragment with a pair of PCR oligonucleotide primers represented by a forward primer of SEQ ID NO:1 and a reverse primer of SEQ ID NO:2 and planting triploid watermelon seeds for which said marker has been identified.

After the triploid is planted, the plants are allowed to grow until harvesting. In some embodiments, the harvesting is about 35 to about 45 days after flowering.

As indicated above, pollination may be insect pollination or hand pollination. In accordance with some embodiments, the pollination is hand pollination. Pollination occurs in anthesis (anthesis is the period during which a flower is fully open or sexually functional). The male flowers are collected and the pollen spread on the female flower stigma by hand. In some other embodiments, pollination is by insects (mostly bees).

In some embodiments, the method requires emasculating the female parent tetraploid watermelon prior to pollination and the triploid hybrid watermelon plant prior to pollination.

In the description above and below the watermelon plant is referred to either by an internal identification code or by a deposit Accession No. For each of reference, the following provides a correlation between the internal reference/name and the NCIMB deposit Accession No.

| | Internal reference/name | Accession No. | Date of deposit |
|---|---|---|---|
| Triploid | S12-12.701 | NCIMB 42044 | 24 Aug. 2012 |
| Triploid | 12.704bPMI-W12 | NCIMB 42172 | Oct. 14, 2013 |
| Triploid | 12.702b-W14 | NCIMB42359 | Feb. 16, 2015 |
| Triploid | 12.135b-W14 | NCIMB42360 | Feb. 16, 2015 |

DESCRIPTION OF SOME NON-LIMITING EXAMPLES

Example 1: Production of Mini Seedless Triploid Watermelons

The target of this breeding was to develop mini seedless watermelon hybrids tolerant to PM, using the genetic background of PI 482312. Unless otherwise stated, all breeding stages were conducted in plastic greenhouses in Bnei Darom, Israel.

The Male Parent Lines

PI 482312 is a watermelon (*Citrullus lanatus* var. *Citroides*) line known to have tolerance to powdery mildew (PM). This PI was obtained from the plant genetic resources unit, Griffin, Georgia, originally from Zimbabwe. PI 482312 exhibited heterogeneity in PM tolerance. Therefore, selections of self pollination of this PI line was conducted to obtain a line homogeneous for high level of PM resistance (i.e. in a scale of between 1 to 10, to a level of 8-9), and this line is referred to herein as PI 482312. To this end, the plants of PI 482312 were routinely grown in plastic greenhouse during the years 2005-2012, in two seasons per year, winter and summer During the routine growth, observations (including microscopic) revealed that resistance of the self pollinated plant showed no symptoms or very minor symptoms.

Figure 2D:
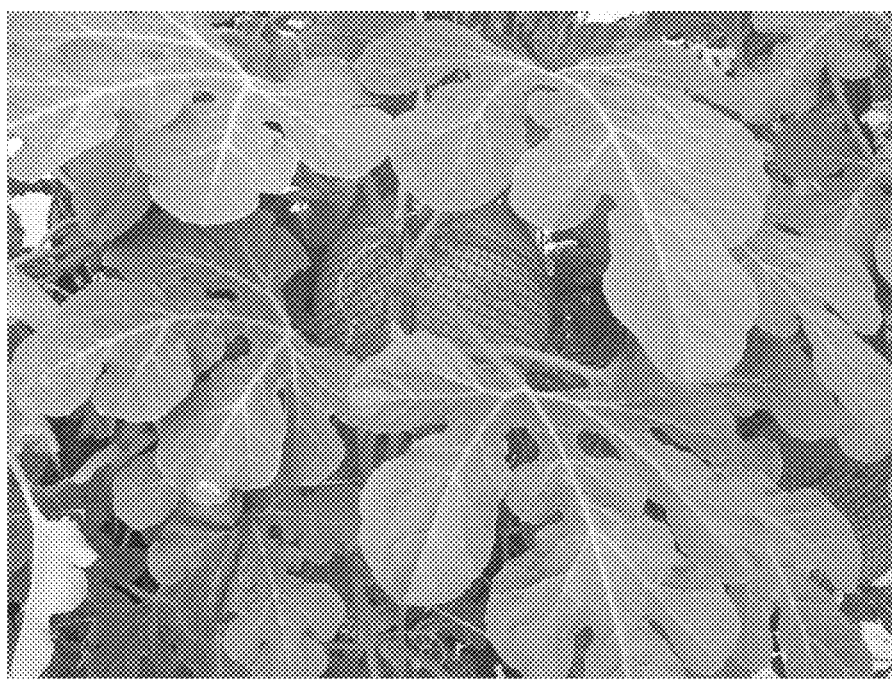

The original plant, PI 482312, is also characterized by a large fruit of about 10 kg, having a gray rind with non-continuous ("broken") green stripes (FIG. 2A), white to yellow fruit flesh (FIG. 2B) and non-bitter taste, Total soluble solids (TSS) of 6% in average. The seeds color is light green and big (about 8 mm*13 mm) (FIG. 2C). PI 482312 plants are PM tolerate, ranked 9, (FIG. 2D).

Development Stases (Year Description):

The target of this breeding was to develop seedless watermelon hybrids tolerant to PM, using the genetic background of PI 482312. Unless otherwise stated, all breeding stages were conducted in plastic greenhouses in the southern areas of Israel.

In the following the breeding lines were exposed to PM where those showing best tolerance were selected. Specifically, the plants were grown in greenhouse and were inoculated by spreading uniformly the fungus by hand in the greenhouse. Also, the plants in the greenhouse were not treated with fungicides. In a scale from 1 to 9 (9 being the best performance of PM tolerance), the four male parent lines exhibited tolerance to PMW1 of 7-8. Three male parent lines exhibited tolerance to PMW2 of 7-8.

The breeding pathways which are also illustrated in Tables 1A-1C below are as follows.

Pathway A (403, 433 &539 PM Tolerance Selection):

Summer 2005: a first cross between PI 482312 and diploid inbred watermelon line "CLS" (selection from Cal sweet variety), as a cultured diploid line, created line "403" (PI×CLS). Each cross and breeding line were exposed to PM and the most tolerant plants were selected for further breeding. The plants were grown in greenhouse and were inoculated by spreading uniformly the fungus by hand in the greenhouse. Also, the plants in the greenhouse were not treated with fungicides.

Winter 2005: a backcross between line "403" and a mini diploid inbred watermelon line "126" (proprietary of Origene Seeds Ltd.) created line "433" (403×126).

Summer and winter 2006: the first generation cross of line "433" namely "433-F1" was self-pollinated two generations to provide F3 generation, namely, "433-F3".

Summer 2007: a backcross between "433-F3" and a mini diploid inbred watermelon line "112" (proprietary of Origene seeds Ltd.) create line "539".

Winter 2007-Summer 2009: the first generation of "539", namely, "539-F1" was promoted four generations to provide F5 generation, namely, "539-F5" (hereinafter, referred to as "509-F5-539-1" for Summer 09, 5$^{th}$ generation of 539).

Winter 2009: a cross between S09-F5-539-1 and a tetraploid female line W11-F99-448-B1 (proprietary of Origene seeds Ltd.) created a first generation, F1, of seedless hybrid_tolerant to PM. This F1 generation was referred to as "W09-9701".

Pathway B (406&554 PM Tolerance Selection):

Summer 2005-Winter 2007: two diploid lines "237" and "406" were promoted separately five generations, with "406" being PM resistant (PMR) and "237" being PM sensitive (PMS). Both lines are diploid inbred watermelon, both a proprietary Origene. The offspring of the five generation, i.e. "237-F6" and "406-F6" were obtained in Winter of 2007.

Each cross and breeding line were exposed to PM and the most tolerant plants were selected for further breeding.

Summer 2008-Summer 2011: a cross between "237-F6" and "406-F6" took place, to create a new diploid male line "554-F1". The "554-F1" was then promoted 3, 4, 5, 6 and 7 generations to provide, respectively, the plants "554-F4" (also referred to as "W09-F4-568-1"), "554-F5" (also referred to as BD10-F5-151-13), "554-F6" (also referred to as W10-F6-642-1) and "554-F7" (also referred to as S11-F7-548-1).

Winter 2009: Crossing between the tetraploid female line W11-F99-448-B1 and the diploid male line "554-F4" to obtain in the Summer of 2010 an improved seedless hybrid tolerant to PM, which was referred to as "S10-9701i", the improvement being in terms of better tolerance to PM as compared to male lines "S09-F5-539-1".

Summer 2010: Crossing between the tetraploid female line W11-F99-448-B1 and the diploid male line "554-F5" to obtain in the Winter of 2010 an improved seedless hybrid tolerant to PM which is referred to as "W10-9701i=10.720", the improvement being in terms of better tolerance to PM as compared to male lines "554-F4" to "554-F5".

Summer 2011: Crossing between the tetraploid female line W11-F99-448-B1 and the diploid male line "554-F7" (also referred to as "S11-F7-548-1") to obtain in the Winter of 2011 an improved seedless hybrid tolerant to PM which is referred to as "W11-10.720", the improvement being in terms of better tolerance to PM as compared to male lines "554-F5" to "554-F7".

Pathway C (572 PM Tolerance Selection):

With the aim to improve the quality of the diploid male line "554-F5" ("BD10-F5-151-13") with horticultural traits such as fruit regularity, smaller fruit and deeper red flesh, a third breeding pathway was employed.

Summer 2010: Backcross of "554-F5" with a diploid inbred watermelon line "112" (proprietary line of Origene Seeds Ltd.) to create male line "572-F1".

Winter 2010-Winter 2011: The line "572-F1" was promoted three generations to "572" (also referred to as "W11-768-B").

Each cross and breeding line were exposed to PM and the most tolerant plants were selected for further breeding.

Winter 2011: Crossing between male line "572" (this line was marked under the name "W11-768-B") and the tetraploid female line W11-F99-448-B1 to obtain in the Summer of 2012 an improved F1 seedless hybrid referred to as "S12-12.701"

TABLE 1A

Breeding pathway A

| Season, year | Female (♀) | Male (♂) | Hybrid (F1) | Male PM selection |
|---|---|---|---|---|
| Summer, 2005 | | 403-F1 (PI* × CLS) | | + |
| Winter, 2005 | | 433-F1 (403 × 126) | | + |
| Summer, 2006 | | 433-F2 | | + |
| Winter, 2006 | | 433-F3 | | + |
| Summer, 2007 | | 539-F1 (433 × 112) | | + |
| Winter, 2007 | | 539-F2 | | + |
| Summer, 2008 | | 539-F3 | | + |
| Winter, 2008 | | 539-F4 | | + |
| Summer, 2009 | W11-F99-448-B1 | 539-F5 (S09-F5-539-1) | | + |
| Winter, 2009 | | | W09-9701 | |

*PI denotes PI 482312

TABLE 1B

Breeding pathway B

| Season, year | Female (♀) | Male (♂) | Hybrid (F1) | Male PM selection |
|---|---|---|---|---|
| Summer, 2005 | | 237-F1, 406-F1 (601F × PI*) | | + |
| Winter, 2005 | | 237-F2, 406-F2 | | + |
| Summer, 2006 | | 237-F3, 406-F3 | | + |
| Winter, 2006 | | 237-F4, 406-F4 | | + |
| Summer, 2007 | | 237-F5, 406-F5 | | + |
| Winter, 2007 | | 237-F6, 406-F6 | | + |
| Summer, 2008 | | 554-F1 (237-F6 × 406-F6) | | + |
| Winter, 2008 | | 554-F2 | | + |
| Summer, 2009 | | 554-F3 | | + |
| Winter, 2009 | W11-F99-448-B1 | 554-F4 (W09-F4-568-1) | | + |
| Summer, 2010 | W11-F99-448-B1 | 554-F5 (BD10-F5-151-13) | S10-9701i | + |
| Winter, 2010 | | 554-F6 (W10-F6-642-1) | W10-9701i = 10.720 | + |
| Summer, 2011 | W11-F99-448-B1 | 554-F7 (S11-F7-548-1) | | + |
| Winter, 2011 | | | W11-10.720 | |

*PI denotes PI 482312

TABLE 1C

Breeding pathway C

| Season, year | Female (♀) | Male (♂) | Hybrid (F1) | Male PM selection |
|---|---|---|---|---|
| Summer, 2010 | | 572-F1 (554-F5 × 112) | | + |
| Winter, 2010 | | 572-F2 (W10-F2-646-1) | | + |
| Summer, 2011 | | 572-F3 (S11-F3-553-d) | | + |
| Winter, 2011 | W11-F99-448-B1 | 572-F4 (W11-F4-768-B) | | + |
| Summer, 2012 | | | S12-12.701 | |

Characterization of Male Parent Lines:

The male parent lines were characterized by the following parameters:

Fruit:
round;
gray rind color (at times showing thin, light green stripes) with thickness of 10 mm in average;
red to deep red flesh;
rind firmness of 10, namely, with low tendency of cracking;
good taste (total soluble solids being in average 11%)

Seeds:
brown color;

PM Tolerance to Resistance:

In a scale from 1 to 9 (9 being the best performance of PM tolerance), the four male parent lines exhibited tolerance to PMW1 of 7-8, and three male parent lines exhibited tolerance to PMW2 of 7-8.

Flowering:

The plants of all four lines flower in the early season. The flowers are monoecious. In a scale from 1 to 90 (90 being the best performance), the four parent males lines exhibited strong plant vigor of 70.

In overall and as evident from Table 2, all male lines commonly share the same characteristics, but still differ in some, including fruit size (weight), flesh color and seed size (Thousand Seeds Weight, TSW). Some differences also appeared in the level of tolerance to PM.

TABLE 2

Characteristics of male lines and the selected female 367-1:

| Characteristics | PI482312-PMR W11-F99-701-1[1] | 539-F5 (S09-F5-539-1) | 554-F5 (BD10-F5-151-13) | 554-F7 (S11-F7-548-1) | 572-F4 (W11-F4-768-B) | 367-1 (W11-F99-448-B11) |
|---|---|---|---|---|---|---|
| Vigor | 90 | 70 | 70 | 70 | 70 | 45 |
| Earliness | 90 | 40 | 40 | 40 | 40 | 50 |
| Setting | 20 | 50 | 30 | 30 | 30 | 70 |
| Flower sex | M | M | M | M | M | M |
| Rind color | Citron | Gray | Gray | Gray | Gray | Crimson dark |
| No. fruit/plant[6] | 2 | 3 | 3 | 3 | 3 | 3 |
| Fruit shape | Flat round | Round | Round | Round | Round | Round |
| Fruit regularity | 60 | 60 | 60 | 70 | 80 | 80 |
| Fruit striping | 20%[2] | 10%[3] | 10%[3] | 10%[3] | 10%[3] | 80%[4] |
| Fruit weight (Kg) | 10 | 4 | 8 | 8 | 4 | 3 |
| Flesh color | White to yellow | Red | Red | Red | Deep red | Deep red |
| Flesh firmness | 90 | 70 | 70 | 70 | 70 | 70 |
| Rind thickness (mm) | 15 | 10 | 10 | 10 | 10 | 12 |
| Rind Crack | 10 | 10 | 10 | 10 | 10 | 10 |
| Seed color | Light green | Brown | Brown | Brown | Brown | Brown |
| TSW[5] (gr) | 180 | 24 | 28 | 44 | 48 | 60 |
| Seed size (mm) | 8*13 | 4.5*6.5 (oval) | 4*7 | 5.5*8.5 (oval) | 5.5*8.5 (oval) | 6*9 |
| Taste | Not bitter | Good | Good | Good | Good | Good |
| TSS (Brix %) | 6 | 11 | 11 | 11 | 11 | 11 |
| PMW1 | 9 | 8 | 7 | 8 | 8 | 2 |
| PMW2 | 9 | 2 | 7 | 8 | 8 | 2 |

[1]F99 is a symbol for commercial/end of breeding line
[2]20% indicating Gray rind with incomplete (broken) green stripes that cover about 20% of the fruit's rind;
[3]10% indicating gentle thin (pencil-like) light green stripes;
[4]80% indicating Gray rind with wide dark green stripes that cover about 80% of the fruit's rind;
[5]Weight of 1,000 seeds;
[6]harvesting 35-45 days after pollination Description of the Female Parent The tetraploid female parent line was named S4W11-F99-448-B, and was obtained from a cross between two tetraploids referenced as lines "326" and "330" (both proprietary tetraploid lines of Origene Seeds Ltd.). Upon PM resistance testing, the female line W11-F99-448-B1 was ranked 2 in terms of sensitivity to PM.

The characteristics of W11-F99-448-B1 female line are also provided in Table 2. Generally, the female line produces round shape fruits of an average weight of 3 kg with dark crimson rind color. The rind thickness is 12 mm. The fruits flesh is deep red with 11% TSS. The seeds color is brown, and TSW is 60 g. The plants flower in the middle season.

Description of the Tolerant Seedless Hybrids

Plants of the male parent lines 539 (S09-539-1), 554-F4 (W09-F4-568-1), 554-F5 (BD10-F5-151-13), 554-F7 (S11-F7-548-1), and 572 (W11-768-B) were crossed with the tetraploid female line W11-F99-448-B1 (resulting in a series of PM-tolerant, seedless hybrids named W09-9701, S10-9701i, W10-9701i (10.720), W11-10.720 and S12-12.701.

The characteristics of the hybrid lines are provided in Table 3.

In general, unless otherwise stated, the plants were grown in a plastic greenhouse in Bnei Darom, Israel. Hand pollination took place, and included collection of males flowers from the male diploid plants and brushing the flowers over the flowers on the female tetraploid plants, in the early morning (7:00-11:00 AM).

The F1 generation from crossing between 539 (S09-539-1) and W11-F99-448-B1 (i.e. 539xW11-F99-448-B1) resulted in the W09-9701 hybrid. The W09-9701 hybrid was initially tested for its tolerance to PM, by artificial (hand spreading) inoculation. Tolerance was tested to both PMW1 in early season and PMW2 in late season.

As shown in Table 3, the "W09-9701" hybrid was found to have a high degree of tolerance to PMW1 (ranked 6) but some sensitivity to PMW2 (ranked 2). Namely, the "W09-9701" hybrid was more tolerant to PMW1 than to PMW2.

Improvement of fruit quality (deeper red flesh color and better fruit regularity) was also required. Therefore, an additional crossing took place. Specifically, the hybrids S10-9701i and W10-9701i (10.720) were produced as a result of pollination between the male parent line 554-F4 (W09-F4-568-1) and 554-F5 (BD10-F5-151-13) and the female parent W11-F99-448-B1 namely to produce the hybrids of (554-F4xW11-F99-448-B1) and (554-F5xW11-F99-448-B1).

The W10-9701i hybrid was tested in an open field in Israel and was also found to have tolerance to both PMW1 and PMW2 (ranking 6 for both pathogens). In addition, the W10-9701i hybrid had an exceptional fruit quality in terms of flesh color (deeper red) and a higher total soluble solids percentage in the fruit (11.5%).

Figure 3:
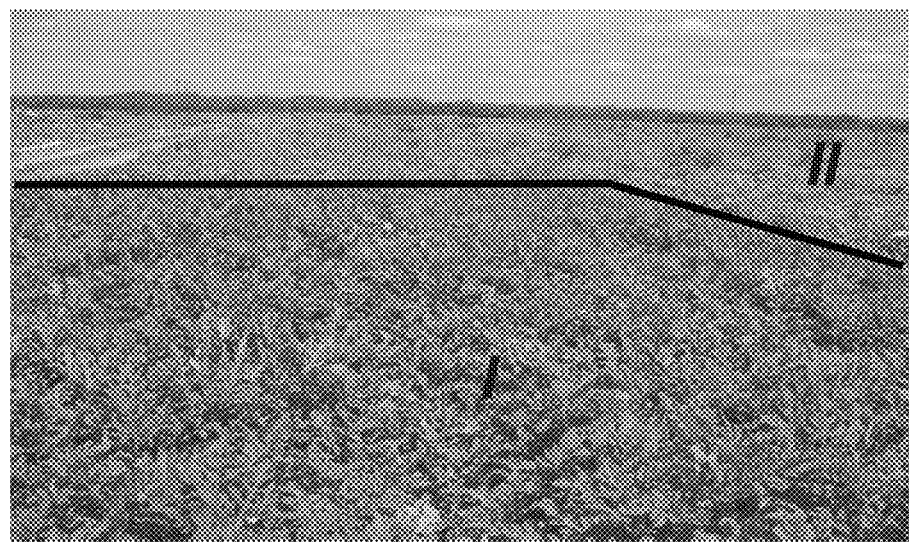
FIG. 3 is an image of a triploid watermelon hybrid according to the present disclosure after exposure to PMW1 and PMW2 (area marked "I" in the field) as compared to a reference seedless watermelon (area marked "II" in the field).
Figure 4:
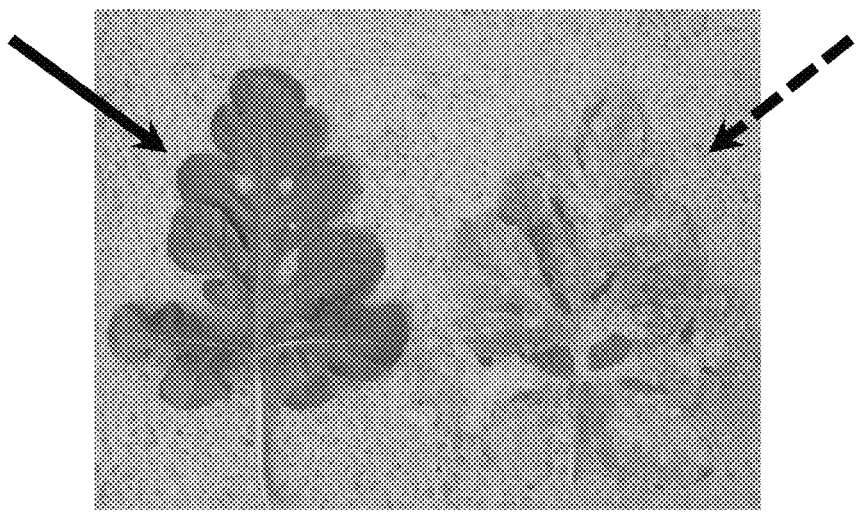
FIG. 4 is an image of leaves of a PM tolerant seedless watermelon according to the present disclosure after exposure to PMW1 and PMW2 (marked by a full arrow) as compared to an infected PM sensitive reference seedless watermelon (marked by a dashed arrow).

The tolerance of the W10-9701i hybrid was also tested in an open field in Brazil, and was found to have high tolerance to both strains of PM (PMW1 and PMW2) as compared to a reference seedless watermelon hybrids (known by the commercial name Leopard (Hazera Israel) tested in the same field, as shown in FIG. 3. Further, FIG. 4 clearly shows that the tolerant watermelon plant after inoculation lacks white mycelium and white spores on both sides of the leaves (full arrow) which are evident on the reference plant (dashed arrow).

Figure 5A:
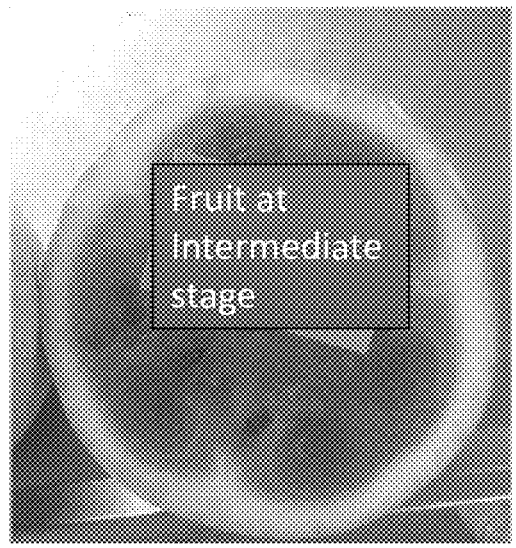
FIGS. 5A and 5B are images of a watermelon fruit of a diploid male parent during selection stages, FIG. 5A showing a fruit of a diploid male parent at intermediate flesh and rind uniformity stage and FIG. 5B at a more progressed flesh and rind uniformity and quality stage.
Figure 5B:
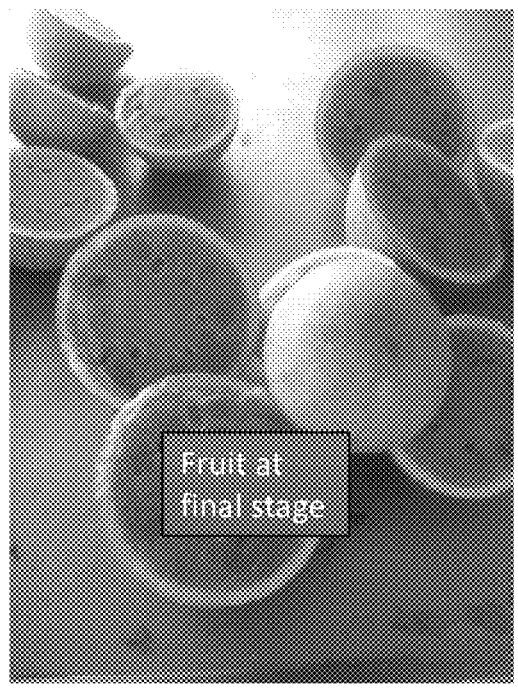

Additional hybrids were produced by hand pollination between the male parent line 554-F7 (S11-F7-548-1) and the same female parent W11-F99-448-B1 (554-F7xW11-F99-448-B1) to produce the hybrid W11-10.721. Also, crossing was between male parent line 572 (W11-768-B) and again the female parent W11-F99-448-B1 (572-F4x W11-F99-448-B1) to produce the hybrid S12-12.701. In this connection, FIGS. 5A and 5B show fruit quality, in particular fruit rind thickness and flesh color uniformity of a fruit at intermediate stage of development (FIG. 5A, corresponding to male line 554 in terms of flesh color uniformity), and of a later line, from which the triploid seedless watermelon of the invention may be produced (FIG. 5B, corresponding to male line W11-768-B, in terms of flesh color uniformity). Specifically, FIG. 5B shows the rind being thin and the flesh being uniform.

As shown in Table 3 all the hybrid lines had a dark crimson rind color and the fruits were essentially round. The weight of the fruits was between 3 to 4.5 Kg and all hybrids showed high tolerance to PMW1, the tolerance ranged 6-7 out of 9.

Winter 2005 till winter 2007: The line "406-F1" was self pollinated five generations to provide F6 generation, namely "406-F6".

Each generation was exposed to PM and the most tolerant plants were selected for further breeding. The plants were grown in greenhouse and were inoculated by spreading uniformly the fungus by hand in the greenhouse. The plants in the greenhouse were not treated with fungicides at all. In parallel each generation was selected for big fruit size being greater than 7 Kg (about 10-14 kg) and quality flesh traits including uniform flesh color of red to deep red, TSS between 11%-12%.

Summer 2008: a backcross between "406-F6" and a small (2-3 Kg) diploid inbred watermelon line "237-F6" (proprietary of Origene seeds Ltd.) created the line "554-F1".

TABLE 3

Characteristics of the triploid hybrid lines

| Hybrid line | W09-9701 | S10-9701i | W10-9701i (10.720) | W11-10.720 | S12-12.701 |
|---|---|---|---|---|---|
| Vigor | 50 | 50 | 50 | 50 | 50 |
| Earliness | 50 | 50 | 50 | 45 | 45 |
| Setting | 50 | 50 | 50 | 50 | |
| Flower sex | M | M | M | M | M |
| Rind color | Dark crimson | Dark crimson | Dark crimson | Dark crimson | Dark crimson |
| No. fruit/plant | 2 | 2 | 2 | 2 | 2 |
| Fruit shape | Round | Round | Round | Round | Round |
| Fruit regularity | 65 | 65 | 65 | 70 | 80 |
| Fruit striping | 80%[1] | 80%[1] | 80%[1] | 80%[1] | 80%[1] |
| Fruit weight (Kg) | 3.3 | 4.5 | 4.5 | 4.5 | 3.2 |
| Flesh color | Light red | Light red | Red | Red | Deep red |
| Flesh firmness | 70 | 70 | 70 | 70 | 70 |
| Rind thickness (mm) | 12 | 12 | 12 | 12 | 12 |
| Rind Crack | 10 | 10 | 10 | 10 | 10 |
| Seed color | Seedless | Seedless | Seedless | Seedless | Seedless |
| Taste | Good | Good | Good | Good | Very good |
| TSS (Brix %) | 11 | 11.5 | 11.5 | 11.5 | Not tested yet |
| PMW1 | 6 | 6 | 6 | 7 | 7 |
| PMW2 | 2 | 6 | 6 | 7 | 7 |

[1]Gray fruit with wide dark green stripes that cover 80% of the fruit

Example 2: Production of Triploid Mini Seedless Watermelon with PM Tolerance—Development Stages (Year Description)

The target of this breeding was to develop seedless watermelon hybrids tolerant to PM, using the genetic background of PI 482312 as described above. Unless otherwise stated, all breeding stages were conducted in plastic greenhouses in the southern areas of Israel. Breeding stages were similar to those described in Example 1 above.

The following breeding lines were exposed to PM and those showing best tolerance were selected (by scoring, see below). Specifically, the plants were grown in a greenhouse and were inoculated by spreading uniformly the fungus by hand in the greenhouse. The plants in the greenhouse were not treated with fungicides at all. In a scale from 1 to 9 (9 being the best performance of PM tolerance), the male parent line exhibited tolerance to PMW1 of 7-8 and three male parent line exhibited tolerance to PMW2 of 7-8.

The breeding pathway is also illustrated in the following Table 4 below.

12.704bPMI (Classico2 Type PMI*) Pathway (Males 406, 554 & 573 PM Tolerance Selection):

Male:
Summer 2005: a first cross between PI 482312 and diploid inbred watermelon line "601F" (proprietary of Origene seeds Ltd.), created the line "406-F1" (601FxPI).

Winter 2008 till summer 2010: The line "554-F1" was self pollinated four generations to provide F5 generation, named "554-b-1-1" ("554-F5"). The plants were grown in greenhouse and were inoculated by spreading uniformly the fungus (by hand) in the greenhouse. The plants in the greenhouse were not treated with fungicides at all.

Summer 2010: Another backcross between "554-F5" and a small (1-2 Kg) diploid inbred watermelon line "216-a-2-B-5-B" ("216-F11") (proprietary of Origene seeds Ltd.) created the line "573-F1".

Summer 2010 till summer 2013: The line "573-F1" was self pollinated seven generations to provide F7 generation, namely "573-r-1-2-1-B" (PMS13-642-B1). Representative generation F5 (PM S12-F5-378-2).

Each cross and breeding line were exposed to PM and the most tolerant plants were selected for further breeding. The plants were grown in greenhouse and were inoculated by spreading uniformly the fungus by hand in the greenhouse. The plants in the greenhouse were not treated with fungicides at all.

Triploid:
Winter 2012: a cross between PMS12-F5-378-2 and a tetraploid female line W11-F99-448-B1 (proprietary of Origene seeds Ltd. created a first generation, F1, of seedless hybrid tolerant to PM. This F1 generation was referred to as "12.704bPMI-W12" ("Classico2 type PMI", PMI indicating tolerance of 6-7). This F1 generation of the seedless tolerant triploid hybrid watermelon was deposited on Oct. 14, 2013, under Accession No. NCIMB 42172.

TABLE 4

12.704b PMI (Classico type PMI) Breeding

| Season, year | Female (♀) | Male (♂) | Hybrid (F1) | Male PM selection |
|---|---|---|---|---|
| Summer, 2005 | | 406-F1 (601F × PI*) | | + |
| Winter, 2005 | | 406-F2 | | + |
| Summer, 2006 | | 406-F3 | | + |
| Winter, 2006 | | 406-F4 | | + |
| Summer, 2007 | | 406-F5 | | + |
| Winter, 2007 | | 406-F6 | | + |
| Summer, 2008 | | 554-F1 (406 × 237-F6) | | + |
| Winter, 2008 | | 554-F2 (W08-F2-554-B) | | + |
| Summer, 2009 | | 554-F3 (554-b, S09-F3-280-2) | | |
| Winter, 2009 | | 554-F4, 554-b-1, W09-F4-568-1) | | + |
| Summer, 2010 | | 554-F5 (554-b-1-1 S10-F5-151-1) | | + |
| | | 573-F1 (554-F5 × 216-F11) | | |
| Winter, 2010 | | 573-F2 (W10-F2-647-B) | | + |
| Summer, 2011 | | 573-F3 (573-r, BD11-F3-555-r) | | + |
| Winter, 2011 | | 573-F4 (573-r-1, PMW11-F4-782-1) | | + |
| Summer, 2012 | | 573-F5 (573-r-1-2, PMS12-F5-378-2) | | + |
| Winter, 2012 | W11-F99-448-B1 | 573-F6 (573-r-1-2-1, PMW12-F6-625-1) | | + |
| | W11-F99-448-B1 | 573-F5 (573-r-1-2 PMS12-F5-378-2) | 12.704bPMI-W12 | |
| Summer, 2013 | | 573-F7 (573-r-1-2-1-B1 PMS13-F7-642-B1) | | + |
| Winter, 2013 | W11-F99-448-B1 | 573-F7 (573-r-1-2-1-B1 PMS13-F7-642-B1) | 12.704bPMI-W13 | |

*PI denotes PI-482312-PMR

TABLE 5

Characteristics of male line "573-r-1-2", female line 367-1 and first generation hybrid 12.704bPMI-W12 (NCIMB 42172):

| Line characteristics | 573-r-1-2 PMS12-F5-378-2 | W11-F99-448-B1 | 12.704b |
|---|---|---|---|
| Vigor | 50 | 45 | 50 |
| Earliness | 40 | 50 | 40 |
| Setting | 70 | 70 | 70 |
| Flower sex | M | M | M |
| Rind color | Tiger | Crimson dark | Crimson dark |
| No. fruit/plan | 3 | 3 | 3 |
| Fruit shape | 50-60 (round to oval) | 50 (round) | 50 (round) |
| Fruit striping | 25[2] | 80[1] | 70[3] |
| Fruit regularity | 80 | 80 | 80 |
| Fruit weight (Kg) | 2 | 3 | 3 |
| Flesh color | Deep red | Deep red | Deep red |
| Flesh firmness | 70 | 75 | 75 |
| Rind thickness (mm) | 5 | 12 | 10 |
| Rind Crack | 10 | 10 | 10 |
| Seed color | Brown dark | Brown | Seedless |
| TSW (gr) | 24 | 60 | Seedless |
| Seed size (mm) | 1.1 * 0.4 (oval) | 6 * 9 | Seedless |
| Taste | Good | Good | Good |
| TSS (Brix %) | 13 | 11 | 11-13 |

TABLE 5-continued

Characteristics of male line "573-r-1-2", female line 367-1 and first generation hybrid 12.704bPMI-W12 (NCIMB 42172):

| Line characteristics | 573-r-1-2 PMS12-F5-378-2 | W11-F99-448-B1 | 12.704b |
|---|---|---|---|
| PMW1 | 9 | 2 | 7 |
| PMW2 | 8 | 2 | 6 |

*PMI: Tolerance 6-7 (also referred to as intermediate resistance)
[1] 80% indicating Gray rind with wide dark green stripes that cover about 80% of the fruit's rind;
[2] 25% indicating Gray rind with thin dark green stripes that cover about 25% of the fruit's rind;
[3] 70% indicating Gray rind with wide dark green stripes that cover about 70% of the fruit's rind;

Example 3: Further Productions of Triploid Seedless Watermelon with PM Tolerance—Development Stages 12.702b Pathway:

Summer 2008: A cross have been taken with two Origene Seeds proprietary lines: "237a4" being PM sensitive (PMS) and "406" being PM resistant (PMR, described hereinabove) to create the line "554-F1".

Summer 2010: A backcross between "554-F5" and Origene Seeds proprietary line "112" (described hereinbefore) was made to create "572-F1".

Winter 2012: A cross between the diploid line "572-b-F5" (PMR) as a male and Origene Seeds Proprietary tetraploid line "612a" (PMS) as a female to create the triploid hybrid "12.702b". This hybrid was created also in winter 2014 with "572-b-F9" and "612a" and was deposited under NCIMB 42359.

12135b Pathway:

Summer 2007: A cross have been made with two Origene Seeds proprietary lines: "ZGM" being PM sensitive (PMS) and "406" being PM resistant (PMR) to create the line "538-F1".

Winter 2010: A second backcross have been made between "538v2-F7" and Origene Seeds proprietary line "523t-F7" to create the male line "675-F1".

Winter 2014: A cross between the diploid male line "675-b2-F8" (PMR) and the Origene Seeds proprietary female line "642b11-1-F12" (PMS) to create the hybrid "12.135b".

Example 4: Sequence Related Amplification Polymorphism (SRAP) Analysis

In order to investigate heritage of the tolerance or resistance to PM from the male parent to the triploid hybrid watermelon plant, the conservation of the trait locus among the various watermelon male parent was analyzed using the SRAP technology and various combinations of primer pairs known in the art (see Table 2 in Levi et al. 2006).

The amplified DNA fragments were separated by denaturing acrylamide gels and detected by autoradiography. Among the various combinations, the combination me1em1 identified a 480 bp locus in all the male parents tested, including W11-701-1, 572 (W11-768-B) (as well as in the other, male diploids disclosed herein) but was missing from cultivated male diploid watermelon plants sensitive to PM.

The invention claimed is:

1. A seedless triploid watermelon plant, a seed that produces said plant, or a fruit of said plant,
wherein said plant contains in its genome a 480 bp locus identifiable when using SEQ ID NO: 1 and SEQ ID NO:2 as forward and reverse PCR primers, respectively,
said plant being selected from the group consisting of
line S12-12.701, having representative seeds that produce said S12-12.701 plant deposited under Accession No. NCIMB 42044;
line 12.704bPMI-W12, having representative seeds that produce said 12.704bPMI-W12 plant deposited under Accession No. NCIMB 42172;
line 12.702b-W14, having representative seeds that produce said 12.702b-W14 plant deposited under Accession No. NCIMB 42359; and
line 12.135b-W14, having representative seeds that produce said 12.135b-W14 plant deposited under Accession No. NCIMB 42360.

2. The plant of claim 1, wherein said plant is a plant of line S12-12.701.

3. The plant of claim 1, wherein said plant is a plant of line 12.704bPMI-W12.

4. The plant of claim 1, wherein said plant is a plant of line 12.702b-W14.

5. The plant of claim 1, wherein said plant is a plant of line 12.135b-W14.

6. The fruit of claim 1, wherein said fruit is from a plant of line S12-12.701.

7. The fruit of claim 1, wherein said fruit is from a plant of line 12.704bPMI-W12.

8. The fruit of claim 1, wherein said fruit is from a plant of line 12.702b-W14.

9. The fruit of claim 1, wherein said fruit is from a plant of line 12.135b-W14.

10. The seed of claim 1, wherein said seed produces a plant of line S12-12.701.

11. The seed of claim 1, wherein said seed produces a plant of line 12.704bPMI-W12.

12. The seed of claim 1, wherein said seed produces a plant of line 12.702b-W14.

13. The seed of claim 1, wherein said seed produces a plant of line 12.135b-W14.

* * * * *

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR oligonucleotide forward primer

<400> SEQUENCE: 1
tgagtccaaa ccggata                                                    17

<210> SEQ ID NO 2
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR oligonucleotide reverse primer

<400> SEQUENCE: 2
gactgcgtac gaattaat                                                   18
```